USOO5767519A

United States Patent [19]
Gelbwachs

[11] Patent Number: 5,767,519
[45] Date of Patent: Jun. 16, 1998

[54] AMBIENT-NORMALIZED DIFFERENTIAL ABSORPTION LIDAR SYSTEM AND METHOD

[75] Inventor: Jerry A. Gelbwachs, Hermosa Beach, Calif.

[73] Assignee: The Aerospace Corporation, El Segundo, Calif.

[21] Appl. No.: 611,442

[22] Filed: Mar. 1, 1996

[51] Int. Cl.[6] .................................................. G01N 21/35
[52] U.S. Cl. ................................... 250/372; 250/338.5
[58] Field of Search .............................. 250/372, 338.5, 250/339.11; 356/338, 342

[56] References Cited

PUBLICATIONS

"Calibrated Remote Measurement of $NO_2$ Using the Differential-Absorption Backscatter Technique", W.B. Grant, et al. Appl. Phys. Lett. vol. 24, No. 11, pp. 550–552 (Jun. 1974).

"Calibrated Remote Measurements of $SO_2$ and $O_3$ Using Atmospheric Backscatter", W.B. Grant, et al. J. Appl. Phys.; vol. 46, No. 7, pp. 3019–3023 (Jul. 1975).

"Mobile Lidar System for Environmental Probing", K. Fredriksson, et al. Appl. Opt., vol. 20, No. 24, pp. 4181–4189 (Dec. 1981).

"Differential Absorption Lidar Sensing of Ozone", E.V. Browell Proc. IEEE, vol. 77, No. 3, pp. 419–432 (Mar. 1989).

"Evaluation of the Effects of Mt. Pinatubo Aerosol on DIAL Measurements of Stratospheric Ozone", W. Steinbrecht, et al. J. Geophys. Res., vol. 100, No. D1, pp. 1215–1233 (Jan. 1995).

"Raman DIAL Measurements of Stratospheric Ozone in the Presence of Volcanic Aerosols", T.G. McGee et al. Geophys. Res. Lett., vol. 20, No. 10, pp. 955–958 (May 1993).

*Primary Examiner*—David P. Porta
*Assistant Examiner*—Richard Hanig
*Attorney, Agent, or Firm*—Derrick M. Reid

[57] ABSTRACT

The present system and method employs Differential Absorption Lidar (DIAL) system and method to measure gas concentration within a plume, for example, ozone density with a rocket exhaust plume when large quantities of chlorine and alumina particles are injected directly into the stratosphere by the current fleet of launch vehicles, the system generate on-resonance and off-resonance pulses prior to plume formation for measuring beyond-plume ambient return and on-resonance and off-resonance pulse during plume formation for measuring beyond-plume returns which are normalized to the ambient returns and then ratioed to indicate the absorption effect within-plume to indicate changes in gas concentrations, being well suited for analysis of environmental affect of the exhaust plumes upon the atmosphere, and particularly, for remote sensing of ozone density within the plume of Titan IV launch vehicles, but can be extended to measure other gas concentration from other types of exhaust plumes.

15 Claims, 3 Drawing Sheets

Ambient Normalized Differential Lidar (DIAL) System

Ambient Normalized DIAL Method

FIG. 3

AMBIENT-NORMALIZED DIFFERENTIAL ABSORPTION LIDAR SYSTEM AND METHOD

Statement of Government Interest

The invention was made with Government support under Contract No. F04701-93C-0094 awarded by the Department of the Air Force. The Government has certain rights in the invention.

FIELD OF INVENTION

The present invention relates to Differential Absorption Lidar (DIAL) systems for remote sensing of gas density within a plume which includes particles and gases.

BACKGROUND OF THE INVENTION

Large quantities of chlorine and alumina particles are injected directly into the stratosphere by the current fleet of space launch vehicles. Environmental concerns have been raised over the impact of the rocket exhaust upon the ozone layer. It is estimated that chlorine emission into the fifteen to forty km altitude range by the Titan IV vehicle and the space shuttle is forty-eight tons and seventy-nine tons, respectively, per mission. Active chlorine in the stratosphere is known to rapidly catalyze ozone destruction. Hence, environmental concerns have been raised over the impact of these launches upon the natural ozone layer. Comprehensive chemical and transport models have been constructed to understand rocket exhaust effects in the stratosphere. Recent models predict almost complete ozone depletion in stratospheric tracks that extend over several kilometers and persist for up to a day. However, the size and persistence of the hole are very sensitive to the rate of dissipation of the rocket plume, which is poorly understood at present. Hence, direct measurements of ozone densities are critical to confirm the spatial and temporal evolution of the hole and for model validation. Thus far, observations have been elusive because of the dynamic transient nature of the localized plume coupled with its rather inaccessible location. The only measurement reported to date involved the use of a U-Two aircraft to sample the exhaust of a Titan III rocket. A drop of forty percent in the ozone density at eighteen km was recorded shortly after launch. Local ozone hole sensing using conventional regional ozone monitoring is largely ineffective for routine accurate analysis of temporal exhaust plumes on ozone hole formations. There exists a need to detect ozone density after a launch vehicle passes through the ozone layer.

Generally, there exist a need for system which can analyzed gas density in atmospheric plumes which may comprise various particles and gases. Lidar has proven to be a powerful technique for remote sensing of the atmosphere. A lidar system uses a laser beam for optical sensing of the atmosphere by laser beam illumination of gas molecules which then backscatter the illumination light to provide a distributive return which can be sensed. The lidar system transmits an illumination beam into the atmosphere and then senses backscattered returns from which to infer temperature, gas density, altitude, or other atmospheric characteristics. Improved accuracy and spatial resolution of the lidar system makes it an ideal instrument for atmospheric monitoring. There are a number of well known optical backscattering phenomena including atomic absorption and emission, Raman scattering, Rayleigh and MIE backscattering, among others.

A conventional Differential Absorption Lidar (DIAL) system routinely monitor stratospheric ozone world wide for determining climatological changes. The conventional DIAL system includes a stationary laser transmitter generating two illumination beams, an on-resonance beam and an off-resonance beam, and includes an optical receiver for sensing backscattered returns from the atmosphere. On-resonance and off-resonance wavelengths correspond to respective molecular absorption maxima and minima of the gas. The conventional DIAL method provides average gas concentration over some selected range interval by analyzing lidar backscattered signals from the altitude range of interest for laser wavelengths tuned to on-resonance and off-resonance wavelengths of the gas under investigation.

The conventional DIAL system would seem ideal to measure gas concentration of exhaust plumes. However the exhaust plume is not a constant stationary fixed gas medium. For the example of ozone monitoring in rocket plumes, the exhaust plume is heavily ladened with inorganic chlorine and alumina particles from the combustion of the aluminum-ammonium perchlorate solid propellant. Ozone is depleted by a variety of chemical pathways including some that involve the presence of sunlight and particles. Time diffusion expands the reaction volume creating a funnel shaped depletion zone along the rocket track. The diameter of the depletion zone in the lower stratosphere expands to several kilometers while in the upper range it extends over tens of kilometers. The reaction zone is transported by the stratospheric winds. Due to a lack of vertical mixing on time scales associated with the reaction, portions of the plume at various altitudes are carried along the stratospheric streamlines at different velocities. Thus, the plume appears as a moving bending tube. A stationary ground-based lidar will intercept only a small parcel of the plume with dimensions characteristic of the reaction zone diameter at any instant of time.

The ozone depletion in the rocket exhaust can be compared with routine stratospheric ozone monitoring for climatological change. Both cases require the capability to sensitively and selectively monitor stratospheric ozone with kilometer range resolution. However, climatological studies permit integration times of several hours whereas exhaust plume monitoring necessitates data collection over several minutes while the plume is blown across the line of sight. Hence, an acceptable exhaust plume DIAL system must be able analyze the plume without lengthy integration times.

Recent eruption of volcanoes has prompted lidar monitoring changes in long-term ozone density with new methods to cope with interference from aerosols. Substantially increased aerosol backscattering and extinction after a major volcanic eruption can lead to errors in DIAL measurements of stratospheric ozone. The conventional DIAL method disadvantageously measures in-plume backscatter returns which are highly volatile over wavelengths by being sensitive to particulate backscattering.

Two improved DIAL methods have been developed to provide particulate interference mitigation. Specifically, a Raman-DIAL method and a multiwavelength-DIAL lidar method have been used to extract ozone densities with varying degrees of success from stratospheric regions contaminated with volcanic dust. The Raman-DIAL method requires lengthy integration times in order to compensate for the three order of magnitude reduction in lidar signals at the Raman-DIAL wavelengths compared to the elastic returns. The multiwavelength-DIAL method employs multiple wavelengths, may produce large errors for sharp aerosol layers, and is unproven for alumina particles. In both methods, the particle scattering and extinction in the exhaust plume compared to the volcanic dust is anticipated to be greater and exhibit larger spatial gradients. The above particulate interference mitigation methods are well suited static plume analysis, but may not be successfully applied to measuring in real time ozone depletion in rapidly varying dynamic exhaust plumes.

Acceptable DIAL lidar systems should function subject to dynamic changes of plume conditions. Approximately fifty to eighty tons of alumina oxide particles per launch accompany the injection of inorganic chlorine into the stratosphere in a localized vehicular path creating a plume track. The large quantities of alumina particles dramatically enhance backscattering and contribute to chemical extinction in the plume. DIAL returns are sensitive to extinction, backscatter, and vertical gradients in backscatter coefficients. The optical properties of the alumina particles are important to lidar analysis. Several measurements have been performed on the exhaust particles. The particles tend to be homogeneous alumina spheres. For a Titan III particle distribution at twenty km altitude, the size distribution is a radial gradient with a large number of monomodal particles with mean diameter less than 0.03 um near the plume edge. Closer to the centerline of the plume, the particles have a mean diameter of 0.3 um while the distribution becomes trimodal at the plume center. The particle size distribution may exhibit an altitude variation because particle formation is dependent upon external engine pressure. Hence, there are large uncertainties ascribed to exhaust particle backscatter, extinction, and associated spatial gradients. A atmospheric plume DIAL lidar should be able to provide reliable analysis subject to these uncertainties.

A path integrated DIAL method has used atmospheric backscatter to measure integrated absorption for use in the lower troposphere. This path integrated DIAL method used DIAL returns at the "on" and "off" resonance wavelengths originating from a beyond-plume ambient region. The beyond-plume DIAL returns are ratioed to normalize the returns and to extract the integrated average gaseous density. The path integrated DIAL method has analyzed nitrogen-dioxide, sulfur-dioxide, and ozone samples in a chamber, and nitrogen-dioxide and sulfur-dioxide concentrations were detected in smokestack type plumes. However, the path integrated DIAL method is valid only when the atmospheric backscattering at the DIAL wavelengths are identical. Path integrated DIAL measurements of stratospheric ozone in a rocket plume employing by distal wavelengths, that is, for example, on-resonance and off-resonance wavelengths separated by fifteen percent, would yield large uncertainties making the method impractical for rocket plumes. Hence, on-resonance and off-resonance wavelengths are proximal to each other, that is, for example, separated by less than one percent, to reduce measurement errors. Specifically, the path integrated DIAL method compares the ratio of the "on" resonant power returns to the "off" resonant power returns, both of which includes in-plume backscattering effects as well as in-plume absorption effects. To minimize the backscattering effects, which is wavelength dependent, the "on" and "off" resonant wavelengths must be substantially equal to each other so that the backscattering difference would be negligible, and the resulting ratio can be used to determine absorption and therefore gas concentration.

The path integration DIAL method uses beyond-plume returns for analysis to determine aerosol concentration by measuring absorption attenuation as indicated by beyond-plume backscattering. This path integration DIAL method uses two measurements: in-plume on-resonance, and in-plume off-resonant. The path integration DIAL method computes the normalized ratio of the on-resonance and off-resonance beyond-plume backscattered returns for gas concentrations determined over an integration time. This path integration DIAL method requires proximal wavelengths because the normalized returns are volatile over wavelengths. The path integrate DIAL method requires substantial integration times for average gas density at long ranges using low power lasers and is unsuitable for measuring gas density with dynamic plume moving at long ranges. Hence, a disadvantage of the path integrated DIAL method is the required use of tunable lasers generating beams at proximal wavelengths. Tunable lasers are commercially available only at low power levels. High power lasers, on the other hand, operate at discrete wavelengths. High power lasers which are available at discrete wavelengths. A pair of high power lasers can be operated at substantially separated distal wavelengths, requiring less integration time for a given range. When extrapolating the path integrated DIAL method to large distances, the path integrated DIAL method acquires returns signals by integrating return signal energy over an integration time. The path integrated DIAL method is unsuitable for measuring fast moving dynamic plumes at great distances because the method requires tunable lasers operating at close proximal wavelengths and low power which then requires the corresponding long integration time insufficient for precise measuring long range fast moving plumes.

Hence, there exist a need for a system which can measure gas density within long range fast moving dynamic plume. There also exists a need to determine the impact upon stratospheric ozone by ozone depletion in the exhaust plume of launch vehicles. There also exists a need to rapidly measure gas density in dynamic particulate plumes. Particularly, remote sensing DIAL systems have not been adapted to readily measure gas density within a dynamic long range plume containing particles, such as ozone gas within an exhaust plume from a launch vehicle. Measurement of ozone depletion in a dynamic exhaust plume is limited by the interferences from exhaust particulate backscatter reducing large signals in times commensurate with plume dimensions which may be dissipated by high stratospheric wind velocities. The path integrated DIAL method disadvantageously requires proximal wavelengths and substantial integration times for long range analysis unsuitable for measurement of dynamic exhaust long range plumes. These and other disadvantages are solved or reduced using the present invention.

SUMMARY OF THE INVENTION

An object of the present invention is to measure the stratospheric ozone density in a plume.

Yet another object of the present invention is the use of differential absorption lidar systems for monitoring stratospheric ozone depletion in an exhaust plume.

A further object of the present invention is a method using UV-ozone differential absorption lidar for monitoring stratospheric ozone depletion in an exhaust plume.

Yet a further object of the present invention is to rapidly measure stratospheric ozone depletion in an exhaust plume which may create interferences from exhaust particulate backscatter limiting large signals during the presence of varying plume dimensions dissipated by high stratospheric wind velocities.

The present invention uses a differential absorption lidar (DIAL) system with an ambient-normalized DIAL method for determining gas density within a plume. The ambient-normalized DIAL method uses out-of-plume and in-plume measurements of "on" and "off" resonance returns. The "out-of-plume" measurements are taken for ambient-normalization. "Out-of-plume" measurements are preferably taken prior to plume formation, or near the plume but not through the plume after plume formation, both so as to measure ambient conditions of the beyond-plume atmosphere unaffected by plume formation. During plume formation, "in-plume" measurements are taken. The two "in-plume" measurements are ambient-normalized to the "out-of-plume" measurements for immediate gas concentration determination. Both pairs of in-plume and out-of-plume measurements are beyond-plume measurements of "on" and "off" resonance returns for atmospheric ranges beyond the plume.

Gas concentration within a plume is determined from attenuation due to plume constituents. The attenuation is embedded in elastic lidar returns from altitudes beyond the plume. The change in gas density as manifested in the plume extinction is directly inferred by comparison of DIAL returns measured prior to, that is "out-of-plume", and during, that is, "in-plume", plume formation. Gas concentration is determined by measuring attenuation as indicated by the beyond-plume ambient-normalized backscattered returns. Hence, the present invention uses at least four different beyond-plume returns measurements, "on" resonance and "off" resonance "out-of-plume" measurement, and "on" resonance and "off" resonance "in-plume" measurements.

The ambient-normalized DIAL method enables real-time gas concentration determination and the use of high power lasers operating at substantially distal on-resonance and off-resonance wavelengths. Successive real time "in-plume" measurements may be taken for real time ambient-normalization and concentration profile determination. Using high this method with high power lasers, a lengthy integration time is not required for gas concentration determination. The "out-of-plume" measurement returns are used to compute the ambient-normalized ratios of the "in-plume" backscattered returns for immediate determination of gas concentrations. Each of the ambient-normalized backscattered returns are ratios of an "out-of-plume" ambient returns and "in-plume" returns, which ratios do not include particulate backscatter coefficients which are highly wavelength dependent but includes a particulate absorption coefficient which is considered wavelength insensitive.

The ambient-normalized DIAL method also enables the use of high power lasers operating at substantially distal "on" and "off" resonance wavelengths. The present invention may use distal wavelengths because in-plume backscattering effects are practically eliminated by ambient-normalization and because particulate absorption coefficients are substantially the same at both wavelengths and therefore have a negligible effect.

In the preferred form of the invention adapted for stratosphere ozone density measurements, the ambient-normalized DIAL method uses separated distal 308 nm and 355 nm wavelengths generated by high power lasers for analysis of plumes at great distances exceeding ten KM. In the preferred form, a conventional U-V DIAL measures backscatter returns for determination of ozone depletion in an exhaust plume of a solid rocket motor.

The present method offers advantages through distal lidar wavelengths enabling long range high power laser measurements and real-time concentration determination while being immune from particulate backscatter interference and associated errors. High power laser lidar signals provide strong elastic backscatter returns for rapid accurate measurement. The ambient-normalized DIAL method avoids potential sources of errors when the atmospheric backscattering wavelengths at the DIAL wavelengths are nearly identical. The present invention advances the art by enabling real time measurements using high power lasers for accurate measurements of long range dynamic plumes. These and other advantages will become more apparent from the following detailed description of the preferred embodiment.

DETAILED DESCRIPTION OF THE PREFERRED EMBODIMENT

An embodiment of the present invention is described with reference to the Figures using reference designations as shown in the Figures. Referring to the FIG. 1, laser 10 generate an off-resonance pulse $\lambda_{off}$ on optical path 11 and laser 12 generates an on-resonance pulse $\lambda_{on}$ path 13. The lasers 10 and 12 may be frequency-doubled alexandrite lasers, though other lasers may be used as well. The off-resonance pulse $\lambda_{off}$ is split by optical splitter 14 providing a off-resonance monitoring pulse on optical path 15. The on-resonance pulse $\lambda_{on}$ is split by optical splitter 16 providing an on-resonance monitoring pulse on optical path 17. The on-resonance pulse $\lambda_{on}$ is transmitted to an on-resonance pulse energy monitor 18 through optical path 17. The off-resonance pulse $\lambda_{off}$ is transmitted to an off-resonance energy monitor 20 through optical path 15. The on-resonance pulse $\lambda_{on}$ is transmitted through the splitter 16, and propagates along path 21, is reflected off reflector 24 and is transmitted along path 23 to a dichroic beam splitter 25. Off-resonance pulse $\lambda_{off}$ propagates to the dichroic beam splitter 25 along path 26 from the beam splitter 14. The dichroic beam splitter 25 directs the $\lambda_{on}$ and $\lambda_{off}$ pluses to transmitter optics 28. The transmitter optics 28 directs on-resonance and off-resonance pulses into the atmosphere.

Figure 1:
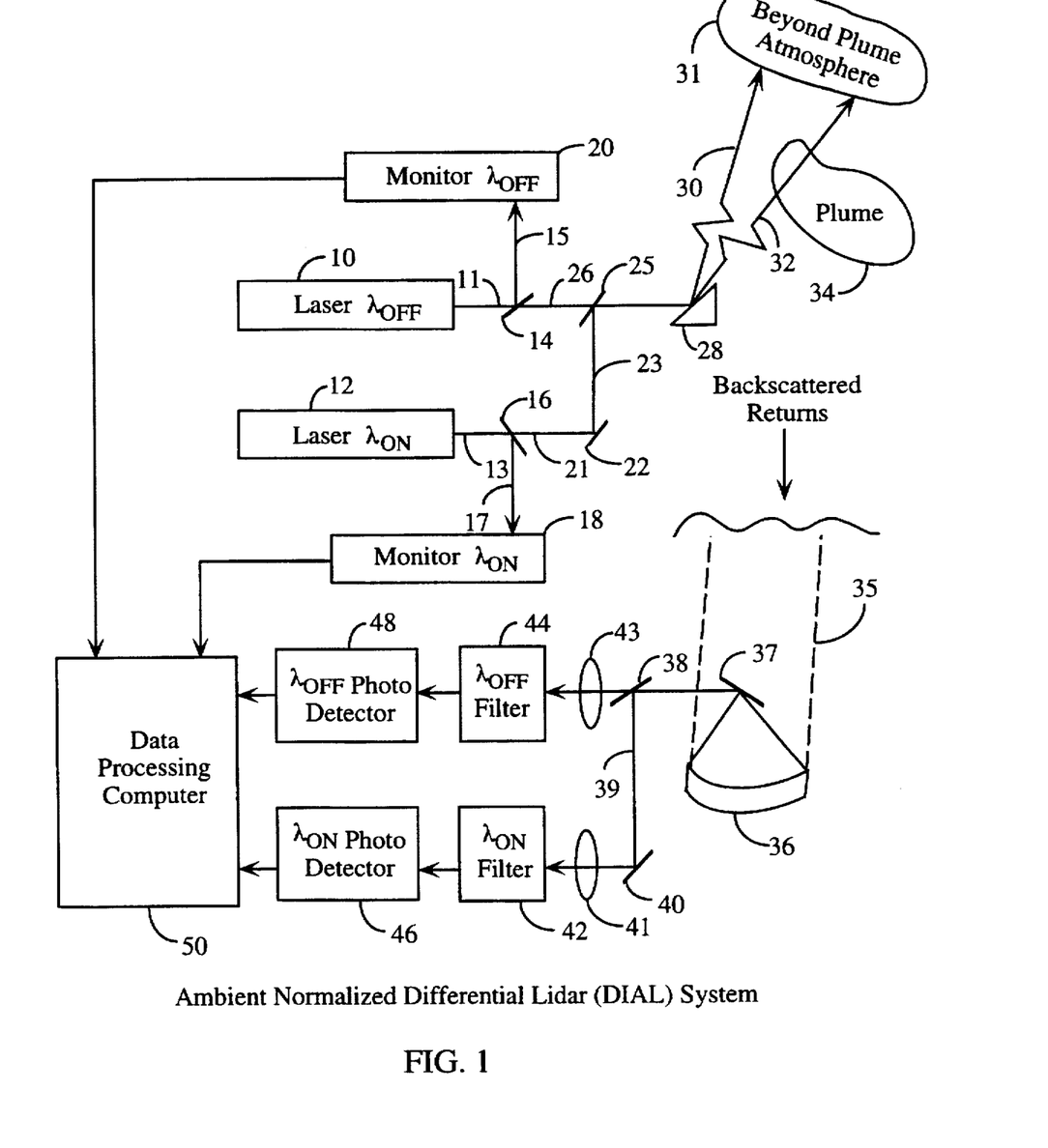
FIG. 1 is a block diagram of an ambient normalized differential lidar (DIAL) system.

The transmitter optics 28 transmits $\lambda_{off}$ pulse along out-of-plume transmission path 30 to a beyond-plume atmosphere 31 and transmits $\lambda_{on}$ pulse along in-plume transmission path 32 which passes through a plume 34 to the beyond-plume atmosphere 31. Path 30 is shown to be out-of-plume during the presence of plume 34. The invention relies upon on-resonance and off-resonance out-of-plume ambient measurements and on-resonance and off-resonance in-plume measurements. The purpose of transmitting pulses out-of-plume along path 30 is to acquire ambient atmosphere measurements while the purpose of transmitting pulses in-plume along path 32 is to acquire plume formation measurements. This enables both in-plume and out-of-plume measurements to be taken substantially concurrently, but requires transmitter optics 28 that can direct the pulse along different transmission paths 30 and 32. Alternatively, path 30 could be coincident with path 32 but requires that ambient atmosphere measurements be taken prior to the formation of the plume 34 after which the plume measurements are then taken. This requires that the in-plume and out-of-plume measurements be taken at substantially different times, for example, prior to launch and after launch of a space rocket, but enables the use of simpler transmitter optics 28 having only one transmission path 32. Transmitter optics 28 having two transmission paths 30 and 32 with concurrent in-plume and out-of-plume measurements is equivalent to transmitter optics 28 having a single path 32 with in-plume and out-of-plume measurements taken at different times. This implementations involve pointing the DIAL system slightly away from the plume 34 along path 30 and then through the plume 34 along path 32. The prior to and during measurements are thereby replaced by concurrent out-of-plume and in-plume measurements along paths 30 and 32, respectively. An advantage of this concurrent out-of-plume measurement is that the duration between measurements can be shortened to fulfill real time temporal stratosphere measurements.

The $\lambda_{on}$ pulses and $\lambda_{off}$ pulses are backscattered by the atmosphere including the beyond-plume atmosphere 31 and by the plume 34, to provide return signals 35 which are received by receiver optics 36 and a receiver mirror 37 which reflects the returns signals 35 to a dichroic beam splitter 38. The splitter 38 separates backscattered return signals 35, including on-resonance and off-resonance return signals. The backscattered returns 35 include a variety of optical signals based upon atmospheric and plume gaseous concentrations and conditions and based upon a plurality of optical interactions. Returns 35 include on-resonance and off-resonance backscattered signals.

On-resonance return signals are reflected from the splitter 38 along path 39 and reflected by reflector 40 through focusing lens 41 onto an on-resonance filter 42 which is a bandpass optical filter only passing on-resonance return signals. Off-resonance return signals are transmitted through dichroic beam splitter 38 and are transmitted through focusing lens 43 onto an off-resonance filter 44 which is also a bandpass optical filter only passing off-resonance return signals. The dichroic beam splitter 38 functions to separate the off-resonance and on-resonance returns signals within respective bands. Focusing lenses 41 and 43 direct the collected backscattered returns collected by the telescope 36 onto an optical filters 42 and 44 which isolate the wavelength returns of interest from the variety of optical signals of the backscattered returns 35. The optical filters 42 and 44 are narrow bandpass filter to isolate backscattered on-resonance and off-resonance return signals. The optical filters 42 and 44 are preferably a narrow bandpass filter centered at on or off-resonance wavelength.

The filters 42 and 44 function to isolate the off-resonance and on-resonance returns signals respectively. Hence, dichroic beam splitter 38 and filters 42 and 44 function together to isolate on-resonance and off-resonance return signals which then illuminate photodetectors 48 and 46, respectively, which function to convert optical on-resonance and off-resonance optical signals into on-resonance and off-resonance return electrical signals which are communicated to a data processing computer 50. The photodetectors 46 and 48 are preferably photomultiplier tubes (PMT) which are illuminated by filtered optical return signals from the optical filters 44 and 42. The photodetectors 46 and 48 convert the optical return signals into electronic signals in the nature of electronic pulse counts. The photodetectors 46 and 48 can be a conventional one inch diameter bi-alkali photocathode PMT that possesses high quantum efficiency and low dark current noise at the on-resonance or off-resonance wavelength. The electronic counts are communicated to a data processing computer 50. The computer 50 also receives on-resonance and off-resonance pulse signals from the pulse energy monitors 18 and 20, respectively. The computer time correlates respective on-resonance and off-resonance pulses to on-resonance and off-resonance returns so as to determine the range of the returns signals 35.

The ambient-normalized differential lidar system of FIG. 1 functions to generate at least two pulses, on-resonance, and off-resonance, at two different times or at two different directions, both for in-plume and out-of-plume measurements, and functions to receive respective returns signals for computer ambient normalized beyond-plume return analysis of gas concentration within the plume 34. For simplicity of construction, the preferred form contains doubled hardware, for examples, dual lasers 10 and 12, dual monitors 18 and 20, dual splitters 14 and 16, dual filters 42 and 44, and dual photodetectors 46 and 48. Such doubled hardware could be redesigned and integrated into a singled hardware configuration. For example, lasers 10 and 11 could be a single laser adapted to generate alternating on-resonance and off-resonance pulses communicated to a single splitter providing both on-resonance and off-resonance reference pulses to a single monitor and to transmitter optics 28 transmitting only along one path. Also, singled hardware units, such as the transmitter optics 28 and receiver 36 could be duplicated and used to receive pulses from respective lasers 10 and 12. The dual and single hardware configurations are equivalent in that both transmit and receive the necessary pulses in-plume and out-of-plume.

The laser 10 and 12 preferably generates an alternating series of pulses of one wavelength and then the other. A series of alternating wavelengths pulses would function equally as well. Each of the transmitted series of pulses illuminate the beyond-plume atmosphere 31 which provides backscattered returns 35 which are optical signals collected by the telescope 36 having a predetermined collection area, for example, one square meter. The electronic pulses are communicated to and analyzed by the computer 50. The computer 50 collects the pulses as photoelectronic counts within time segments corresponding to the entire altitude range, that is, the entire return time period. The monitors 20 and 18 provide reference signals of the on-resonance and off-resonance pulses so that the computer 50 can reference the backscattered on-resonance and off-resonance returns to the transmitted on-resonance and off-resonance pulses for altitude determination and power level calibration. The measured output energy reference from the monitors 20 and 18 serves to calibrate the photocounts of the backscattered returns 20. The time displacement from the transmission of the transmitted pulses to the reception of the returns 20 determines the altitude range for the respective returns 35, while the wavelength of the pulses, that is, the wavelength of the pluses from the laser 10 and 12, reference the returns 35 to respective wavelengths of the transmitted pulses $\lambda_{on}$ and $\lambda_{off}$.

Figure 2:
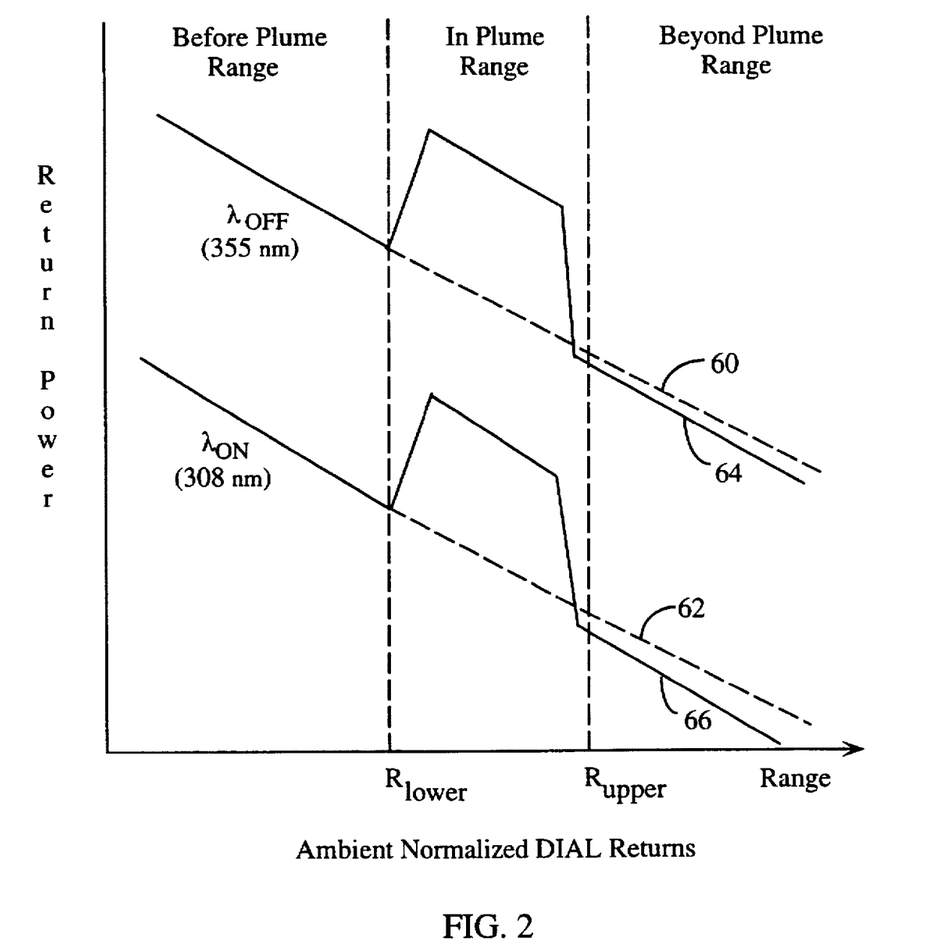
FIG. 2 is a graph diagram of ambient normalized DIAL returns.

When using path integration during return signal acquisition, the returns 35 are collected and converted into electronic pulses which are counted for a predetermined period of time, preferably for example, one millisecond, subsequent to respective transmission of each illumination pulse. The period of time corresponds to the altitude range of interest. The range period time is divided into range time segment periods. Respective electronic counts for each wavelength $\lambda_{on}$ and $\lambda_{off}$ representing the amount of collected photons within the band pass of the optical filters 42 and 44 and detected by the photodetectors 46 and 48, respectively, are accumulated for each range time segment. Each time segment may be characterized as a time segment bin into which is accumulated the number of collected return photons received during that respective time segment bin. Preferably, the time segments are short in duration, for example, one microsecond in duration providing, for example, one thousand time segments over the preferred one millisecond range period. For each of the transmitted pulses, $\lambda_{on}$ or $\lambda_{off}$, the data processing computer 50 compiles photocounts for each of a plurality, e.g. one thousand, of vertically referenced amplitudinal electronic count values, one for each time segment, over the entire horizontally referenced range time period, e.g. one millisecond. For a series of transmitted pulses, for example, ten thousand pulses of the same wavelength, a series of accumulated photocounts are compiled by the data processing computer 50. The cumulative counts for the transmitted wavelengths provides as a backscattered power by range profile as shown in FIG. 2 showing the DIAL returns as return power over altitude range.

Figure 3:
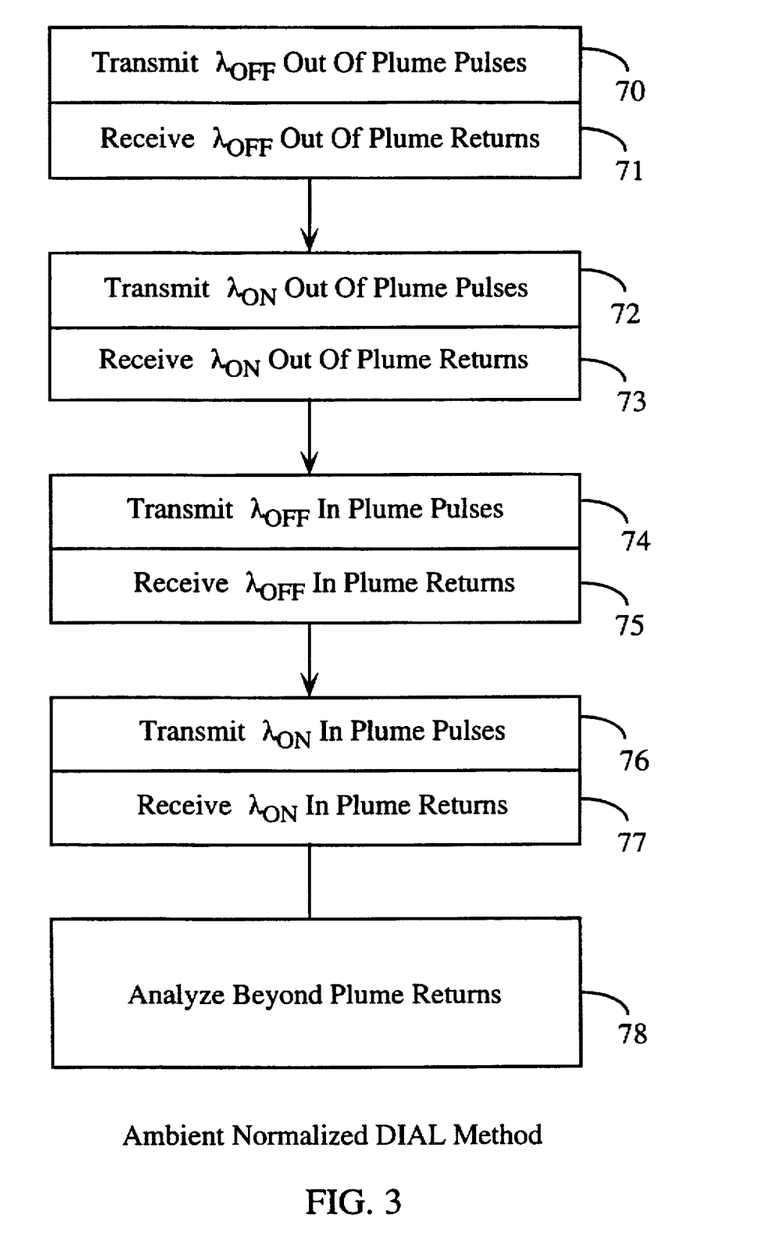
FIG. 3 is a flow diagram of an ambient normalized DIAL method.

Referring to all of the Figures, preferably, the $\lambda_{off}$ and $\lambda_{on}$ out-of-plume measurements 60 and 62, respectively, are taken prior to plume formation. The $\lambda_{off}$ and $\lambda_{on}$ in-plume measurements 64 and 66 are taken after plume formation. All measurements may be along the same optical path 30. DIAL measurements of the beyond-plume atmosphere 31 may be taken by transmitting 70 $\lambda_{off}$ off-resonance out-of-plume pulses and receiving 71 $\lambda_{off}$ off-resonance out-of-plume returns 60, then transmitting 72 $\lambda_{on}$ on-resonance out-of-plume pulses and receiving 73 $\lambda_{on}$ on-resonance out-of-plume returns 62, then transmitting 74 $\lambda_{off}$ off-resonance in-plume pulses and receiving 75 off-resonance in-plume returns 64, then transmitting 76 $\lambda_{on}$ on-resonance in-plume pulses and receiving 77 $\lambda_{on}$ on-resonance in-plume returns 66, and then analyzing 78 the returns 60, 62, 64 and 66. Process step pairs 70 and 71, 72 and 73, 74 and 75, and 76 and 77, may be taken in different order, but are arrange in the preferred sequence. Each transmit step 70, 72, 74 and 76 may be repeated many times, for example, one thousand times as a series of pluses, for computation averaging of receive returns in respective steps 71, 73, 75 and 77, before performing 78 return analysis.

The preferred $\lambda_{on}$ and $\lambda_{off}$ wavelengths are conventional type on-resonance and off-resonance stratospheric ozone DIAL wavelengths, preferably at 308 nm and 355 nm, respectively, illuminating the beyond-plume atmosphere 31 and the plume 34, which may be for example a rocket exhaust plume, for ozone depletion analysis. Measurements are taken of the ambient stratosphere 31 prior to interception of a rocket exhaust plume 34. The out-of-plume measurements 60 and 62 may be taken 70–73 any time prior to launch up to a few minutes before a segment of the plume 34 crosses the optical path 30. As the ozone depleted plume 34 intercepts the lidar beam path 32, enhanced backscatter due to alumina particulate scattering clearly delineates the plume boundaries as shown in FIG. 2. As a result, the lidar plume profile can be divided neatly into three ranges, a before-plume range, an in-plume range and a beyond-plume range. The before-plume range is below a R-lower range. The in-plume range is between the R-lower range and a R-upper range. The beyond-plume range is above the R-upper range.

The before-plume range is below the exhaust plume 34. In the before-plume range, the lidar returns $\lambda_{off}$ 60 and 64, are identical to $\lambda_{on}$ lidar returns 62 and 66, respectively, prior to and after plume formation. However, ozone depletion in the presence of exhaust particles is experienced in the in-plume range as shown by the enhanced backscatter in the plume 34 indicated by increase return power in the in-plume range. The spatial distance of the plume 34 is shown to be the distance between the R-lower and R-upper altitude ranges of the plume 34. Embedded within the returns 64 and 66 is diminished absorption due to ozone reduction in the in-plume range. Above the ozone depletion zone, that is, above the in-plume range, is the beyond-plume range where the stratosphere is assumed to remain undisturbed as an ambient condition.

The general lidar equation takes the form $P(R)=(E/hU)(A/4\pi R2) T \beta(R) L \exp[-2 \partial \alpha(R')dR']$, where P(R) is photodetector received photons at the range R, E is the laser pulse energy, hU is the photon energy, A is the effective receiver aperture, T is the transmission of the receiver optics, $\beta(R)$ is the backscattering coefficient at range R, L is the range interval, $\partial$ is the integral between limits 0 and the range R over the range variable R', and $\alpha$ refers to the extinction coefficient. The equation can be rewritten as $P=K \beta(R) \exp[-2 \partial \alpha(R')dR']$, where K is a constant containing terms that are independent of $\alpha$ and $\beta$.

Prior to the plume 34 intercepting the optical path 32, the received power 60 in the beyond-plume range at the $\lambda_{off}$ wavelength is $P_{off-a}=K_{off} \beta_{off}(R) \exp[-2 \partial \alpha_{off-a} (R')dR']$, where $\alpha_{off-a}$ is the extinction due to the ambient stratosphere. As the lidar pulses propagates into the beyond-plume range, after traversal of the depletion in-plume range, the pulses experiences extinction due to the exhaust particles in addition to ambient extinction. The expression for received power in beyond-plume range through the plume at the "off" wavelength is given by $P_{off-p}=K_{off} \beta_{off}(R) \exp[-2 \partial \alpha_{off-a} (R')dR'-2<\alpha_{off-p}> L_d]$ where $<\alpha_{off-p}>$ is the average value of alumina particle extinction in the in-plume range at $\lambda_{off}$ wavelength and $L_d$ is the spatial distance R-upper minus R-lower. The $\lambda_{off}$ returns are ambient normalized by dividing the $P_{off-p}$ by $P_{off-a}$ that is, $P_{off-p}/P_{off-a}=\exp[-2<\alpha_{off-p}> L_d]$. The ratio of received power above the depletion in-plume range, that is, the beyond-plume range at the "off" wavelength serves to measure integrated particulate extinction.

Lidar signals at the $\lambda_{on}$ wavelength in the beyond-plume range are also ambient normalized in the same way. Prior to plume development, $P_{on-a}=K_{on} \beta_{on}(R) \exp[-2\partial 60_{on-a} (R')dR']$. As the lidar pulse pass through the plume 34 along path 32, the received returns at $\lambda_{on}$ undergo modification by the exhaust particles and ozone reduction. That is, $P_{on-p}=K_{on} \beta_{on}(R) \exp[-2 \partial \alpha_{on-a} (R')dR'-2 <\alpha_{on-p}> L_d+2 <\Delta n>\sigma_{on} L_d]$, where $<\Delta n>$ is the average $<>$ density (n) change $\Delta$, that is, the average ozone density loss in the plume, and $\sigma$ on is the ozone absorption cross section at $\lambda_{on}$. Once again, ratio of the received lidar signals in the presence of the plume is ambient normalized to the ambient returns, that is, $P_{on-p}/P_{on-a}=\exp[-2 (<\alpha_{on-p}>-<\Delta n> \sigma \text{ on}) L_d]$.

The change in ozone density across the plume 34 can be indicated by the ratio of the ambient normalize power returns $P_{on-p}/P_{on-a}$ and $P_{off-p}/P_{off-a}$. That is, $-2 <\Delta n> \sigma_{on} L_d=\ln[(P_{off-p}/P_{off-a})/(P_{on-p}/P_{off-a})]+2 L_d (<\alpha_{off-p}>-<\alpha_{on-p}>)$. The term, $(P_{off-p}/P_{off-a})/(P_{on-p}/P_{off-a})$, is the ratio of lidar returns from above the plume at the two wavelengths normalized to the signals obtained from the ambient stratosphere. The term, $2 L_d (<\alpha_{off-p}>-<\alpha_{on-p}>)$ represents the difference in particle extinction through the plume at the two wavelengths. Because of the wavelength in sensitivity of $\alpha$, this term can be ignored, i.e., $<\alpha_{on-p}>\approx 0$. In the absence of this term, the ozone depletion through the plume can be directly inferred from the signals 60, 62, 64 and 66 in the beyond-plume range.

A similar expression exists for conventional DIAL when the target species is enveloped in an aerosol background, either in the troposphere or in the stratosphere. Particle extinction and backscattering is wavelength dependent. The origin, composition, and size distribution of the particles are different for various man made and naturally occurring aerosols. The α and β values for natural aerosols are different from those of rocket particles.

Two modes of preferred operation for the ambient normalize DIAL method can be applied to monitoring ozone depletion in the plume of a solid rocket motor. The first mode uses measured α and β values for particulate scattering and extinction coefficients and represents the case of mild aerosol interference. The second mode manifests extreme interference effects. Lidar parameters of a conventional UV ozone DIAL technique system may be used. The "on" and "off" wavelengths are 308 and 355 nm, respectively. Lidar system parameters are as follows: E=300 mJ/pulse, thirty Hz repetition rate, A=0.1 m$^2$, T=0.2, and photomultiplier quantum efficiency of thirty percent. LOWTRAN seven data with rural aerosols is used to obtain atmospheric transmission through the troposphere. Ambient ozone density profiles from the U.S. Standard Atmosphere may be used. Ozone absorption cross sections at 308 and 355 nm are $1.2 \times 10^{-19}$ cm$^2$ and $6.3 \times 10^{-23}$ cm$^2$, respectively. Pure molecular backscattering in the stratosphere is assumed. A four km plume segment is intercepted by optical beam 32 directly overhead between twenty and twenty-four km altitude. Complete ozone depletion occur throughout the plume. Representative winds at twenty km altitude overhead are set at approximately forty km/hr. The entire four km plume passes through a fixed lidar beam in about six min.

In the first mode, the lidar beam 32 passes through the plume away from the central core. In this mode, medium particles dominate optical scattering. The value of particulate extinction coefficient may be calculated. The corresponding backscatter coefficient can be calculated for this size distribution. For spherical alumina particles with characteristic dimension near one mm, the lidar ratio is two which yields β=0.001/km-sr. Under the plume, the 355 nm off-resonance beam suffers less attenuation than the 308 nm on-resonance beam as it penetrates the troposphere. The more rapid decay with range of the 308 nm beam compared to the 355 nm signal in the stratosphere is due to the larger ozone absorption and molecular backscattering at the 308 nm wavelength. The presence of the plume is marked by enhanced backscattering. For ranges above the plume, the 355 nm profiles 60 and 64, that is prior to and during plume formation, are barely distinguishable due to the rather small particulate attenuation for this mode, namely, $\sigma_{eff-p}=0.002$/km. The 308 nm profile 66 taken through the in-plume range is distinctively above the prior-to profile 62 because of diminished attenuation due to the depletion of ozone in the twenty to twenty-four km range. The calculated ratio of the two 308 nm profiles 62 and 66 due to the differences in ozone density corresponds to sixty-four percent between twenty and twenty-four km beyond-plume ranges. The ability to distinguish between the two 308 nm profiles 60 and 62 beyond the plume illustrates the benefits of the ambient normalize DIAL method.

The second mode represents the case of particulate interference that is approximately a hundred times more severe than in the first mode. All other parameters are the same. With respect to the 355 nm off-resonance signals, greatly enhanced alumina backscattering is due to heavier particulate loading. In the beyond-plume range, the plume profile 64 is significantly less that the ambient profile 60. There is a clear difference between the two 355 nm lidar returns above twenty-five km. The difference is used to measure the particulate extinction. The two 308 nm on-resonance profiles 62 and 66 resemble the 355 nm off-resonance return profiles 62 and 66, but with two notable exceptions in beyond-plume range. Firstly, in first mode, the 308 nm profile 66 taken through the plume 34 falls well below the ambient profile 62 due to the fact that the magnitude of the particulate extinction is larger than the reduction in attenuation due to ozone depletion. Secondly, the quotient of the two 308 nm on-resonance returns is less than the quotient of the 355 nm off-resonance returns with the difference attributed to decreased ozone absorption in the plume 34.

The ambient normalized DIAL method enables large magnitudes of the lidar return signals. Nitrogen Raman signals are approximately three orders of magnitude below the Rayleigh backscatter from air molecules. Assuming thirty hertz operation and sixty second integration time at each wavelength, the Raman signal levels will be too small to allow for accurate ozone density determination within the plume. Because vertical integration of the lidar returns over many range elements provides larger signal levels than can be acquired from a single range element, the ambient normalized DIAL method offers the potential for obtaining large signal to noise ratios that translates into improved precision for ozone density determination within the plume.

The ambient normalized DIAL method allows for the determination of average concentration along a optical path 32 through a plume 34. A lidar beam along path 32 can scan the plume 34 to image the plume 34 to determine volumetric gas densities. In-plume range data provide for the plume profile, while scanning beams provide for average gas density through the plume 34 at various scanning paths 32.

The present invention relies upon smooth gas absorption coefficients over optical wavelengths. Fine features in the absorption spectrum of a target gas may limit the usefulness of the present invention. Selected on-resonance wavelength should have the same atmospheric interaction, save only the absorption by the target gas within the plume. However, the new ambient normalized method provides greater choice in the selection of suitable on-resonance and off-resonance wavelengths, which may be distal, but otherwise should be as proximal as practicable so to produce the same atmospheric interaction to better isolate the effect of optical absorption by the target gas within the plume for superior measurement precision. With smoother absorption features through varying wavelengths of a gas within a plume 34, the present invention offers a greater choice in wavelengths which may be distal from each other, and which may be measured without lengthy integration times well suited for remote sensing of dynamic plumes.

The preferred ambient normalized DIAL system can be used for remote ozone reduction sensing in a rocket exhaust plume, but can also be applied to other plumes and gases. For example, the ambient normalize method can also be used for measuring sulfur dioxide or nitrogen dioxide concentrations in industrial smoke stack plumes. The above ambient normalized DIAL system and method provide for measurement of gas concentration within a plume by normalizing beyond-plume in-plume returns to corresponding ambient beyond-plume out-of-plume returns. While the preferred system and method may be modified, improved or enhanced, those modifications, improvements and enhancements may nonetheless fall within the spirit and scope of the following claims.

What is claimed is:

1. A differential absorption lidar system comprising a laser means for generating on-resonance in-plume pulses at an on-resonance wavelength and off-resonance in-plume pulses at an off-resonance wavelength, a transmitter means for transmitting on-resonance in-plume pulses and off-resonance in-plume pulses along an in-plume path into an absorbing gas within a plume within an atmosphere, a receiver means for receiving respective backscattered on-resonance in-plume returns and off-resonance in-plume returns, a photodetector means for converting the on-resonance in-plume returns and off-resonance in-plume returns into respective on-resonance in-plume electrical counts and off-resonance in-plume electrical counts, and a processing means for counting the on-resonance in-plume electrical counts and off-resonance in-plume electrical counts over time displaced altitude range and for determining gas concentration of the absorbing gas, wherein the improvement comprises, the transmitter means is also for transmitting on-resonance out-of-plume pulses at the on-resonance wavelength and transmitting off-resonance out-of-plume pluses at the off-resonance wavelength, with both of the out-of-plume pulses transmitted so as to not pass through the plume, the receiver means is also for receiving respective backscattered on-resonance out-of-plume returns and off-resonance out-of-plume returns, with all the returns containing at least respective beyond-plume returns, the photodetector means is also for converting the on-resonance out-of-plume returns and off-resonance out-of-plume returns into respective on-resonance out-of-plume electrical counts and off-resonance out-of-plume electrical counts, and the processing means is also for counting the on-resonance out-of-plume electrical counts and off-resonance out-of-plume electrical counts over time displaced altitude range and for determining the gas concentration from electrical counts from the beyond-plume returns.

2. The lidar system of claim 1 wherein the on-resonance wavelength and off-resonance wavelength are distal wavelengths.

3. The lidar system of claim 1 wherein the out-of-plume path and the in-plume path are identical.

4. The lidar system of claim 1 wherein the processing means ambient normalizes on-resonance in-plume returns and off-resonance in-plume returns from the atmosphere backscattered from beyond the plume by ambient normalized ratios to respective on-resonance out-of-plume returns and off-resonance out-of-plume returns also from the atmosphere backscattered from beyond the gas plume, and determines the gas concentration by ratio of the on-resonance ambient normalized on-resonance ratio to the ambient normalized off-resonance ratio.

5. The system of claim 1 wherein
the atmosphere is an atmosphere of earth,
the on-resonance wavelength and off-resonance wavelength are distal wavelengths, and
the processing means ambient normalizes on-resonance in-plume returns and off-resonance in-plume returns from the atmosphere backscattered from beyond the gas plume by ambient normalized ratios to respective on-resonance out-of-plume returns and off-resonance out-of-plume returns also from the atmosphere backscattered from beyond the gas plume, and determines the gas concentration by ratio of the on-resonance ambient normalized on-resonance ratio to the ambient normalized off-resonance ratio.

6. The system of claim 5 wherein the
the plume is an exhaust plume of particles,
the absorbing gas is ozone,
the on-resonance wavelength is 308 nm, and
the off-resonance wavelength is 355 nm.

7. The system of claim 5 wherein the
the plume is a rocket exhaust plume,
the beyond-plume atmosphere is stratosphere
the absorbing gas is ozone,
the on-resonance wavelength is 308 nm, and
the off-resonance wavelength is 355 nm.

8. A method for measuring gas concentration of an absorbing gas within a plume of particles within an atmosphere, the method comprising transmitting on-resonance out-of-plume pulses at an on-resonance wavelength without passing through the plume for generating on-resonance out-of-plume returns backscattered from the atmosphere at a range beyond the plume, receiving respective on-resonance out-of-plume returns, converting the on-resonance out-of-plume returns into respective on-resonance out-of-plume electrical counts, counting the on-resonance out-of-plume electrical counts over time displaced altitude range, transmitting off-resonance out-of-plume pulses at an off-resonance wavelength without passing through the plume for generating off-resonance out-of-plume returns backscattered from the atmosphere at a range beyond the plume, receiving respective off-resonance out-of-plume returns, converting the off-resonance out-of-plume returns into respective off-resonance out-of-plume electrical counts, counting the off-resonance out-of-plume electrical counts over time displaced altitude range, transmitting off-resonance in-plume pulses at the off-resonance wavelength passing through the plume for generating off-resonance in-plume returns backscattered from the atmosphere at a range beyond the plume, receiving respective off-resonance in-plume returns, converting the off-resonance in-plume returns into respective off-resonance in-plume electrical counts, counting the off-resonance in-plume electrical counts over time displaced altitude range, transmitting on-resonance in-plume pulses at the on-resonance wavelength passing through the plume for generating on-resonance in-plume returns backscattered from the atmosphere at a range beyond the plume, receiving respective on-resonance in-plume returns, converting the on-resonance in-plume returns into respective on-resonance in-plume electrical counts, counting the on-resonance in-plume electrical counts over time displaced altitude range, determining gas concentration of the absorbing gas.

9. The method of claim 8 wherein the on-resonance wavelength and off-resonance wavelength are distal wavelengths.

10. The method of claim 8 wherein the out-of-plume path and the in-plume path are identical.

11. The method of claim 8 wherein the determining steps comprises the steps of ambient normalizing by on-resonance in-plume electrical counts for a range of beyond the plume to on-resonance out-of-plume returns also for a range of beyond the plume into a ambient normalized on-resonance ratio, ambient normalizing by off-resonance in-plume electrical count for a range of beyond the plume to off-resonance out-of-plume returns also for a range of beyond the plume into an ambient normalized off-resonance ratio, and determining the concentration of the absorbing gas from a ratio of the ambient normalized on-resonance ratio to the ambient normalized off-resonance ratio.

12. The method of claim 8 wherein in-plume transmitting, receiving, converting and counting steps are repeated a plurality of times along respective differing in-plume optical paths so as to scans the plume, said method further comprises the step of generating a gas density image of the plume.

13. The method of claim 8 wherein the atmosphere is an atmosphere of earth, the on-resonance wavelengths and off-resonance wavelength are distal wavelengths, and wherein the determining step comprises, ambient normalizing by on-resonance in-plume electrical counts for a range of beyond the plume to on-resonance out-of-plume returns also for a range of beyond the plume into a ambient normalized on-resonance ratio, ambient normalizing by off-resonance in-plume electrical count for a range of beyond the plume to off-resonance out-of-plume returns also for a range of beyond the plume into an ambient normalized off-resonance ratio, and determining the concentration of the absorbing gas from a ratio of the ambient normalized on-resonance ratio to the ambient normalized off-resonance ratio.

14. The method of claim 13 wherein the the plume is an exhaust plume of particles, the absorbing gas is ozone, the on-resonance wavelength is 308 nm, and the off-resonance wavelength is 355 nm.

15. The method of claim 13 wherein the the plume is a rocket exhaust plume, the beyond-plume atmosphere is stratosphere the absorbing gas is ozone, the on-resonance wavelength is 308 nm, and the off-resonance wavelength is 355 nm.

* * * * *

UNITED STATES PATENT AND TRADEMARK OFFICE
CERTIFICATE OF CORRECTION

PATENT NO. : 5,767,519
DATED : June 16, 1998
INVENTOR(S) : Jerry A. Gelbwachs

It is certified that error appears in the above-indentified patent and that said Letters Patent is hereby corrected as shown below:

The title page, showing an incorrect illustrative figure, should be deleted, and substitute therefor the attached title page.

Signed and Sealed this

Twenty-seventh Day of October, 1998

*Attest:*

BRUCE LEHMAN

*Attesting Officer*　　　*Commissioner of Patents and Trademarks*

United States Patent [19]
Gelbwachs

[11] Patent Number: 5,767,519
[45] Date of Patent: Jun. 16, 1998

[54] AMBIENT-NORMALIZED DIFFERENTIAL ABSORPTION LIDAR SYSTEM AND METHOD

[75] Inventor: Jerry A. Gelbwachs, Hermosa Beach, Calif.

[73] Assignee: The Aerospace Corporation, El Segundo, Calif.

[21] Appl. No.: 611,442

[22] Filed: Mar. 1, 1996

[51] Int. Cl.$^6$ .................................................. G01N 21/35
[52] U.S. Cl. ................................... 250/372; 250/338.5
[58] Field of Search ................................. 250/372, 338.5, 250/339.11; 356/338, 342

[56] References Cited

PUBLICATIONS

"Calibrated Remote Measurement of $NO_2$ Using the Differential-Absorption Backscatter Technique", W.B. Grant, et al. Appl. Phys. Lett. vol. 24, No. 11, pp. 550–552 (Jun. 1974).

"Calibrated Remote Measurements of $SO_2$ and $O_3$ Using Atmospheric Backscatter", W.B. Grant, et al. J. Appl. Phys.; vol. 46, No. 7, pp. 3019–3023 (Jul. 1975).

"Mobile Lidar System for Environmental Probing", K. Fredriksson, et al. Appl. Opt., vol. 20, No. 24, pp. 4181–4189 (Dec. 1981).

"Differential Absorption Lidar Sensing of Ozone", E.V. Browell Proc. IEEE, vol. 77, No. 3, pp. 419–432 (Mar. 1989).

"Evaluation of the Effects of Mt. Pinatubo Aerosol on DIAL Measurements of Stratospheric Ozone", W. Steinbrecht, et al. J. Geophys. Res., vol. 100, No. D1, pp. 1215–1233 (Jan. 1995).

"Raman DIAL Measurements of Stratospheric Ozone in the Presence of Volcanic Aerosols", T.G. McGee et al. Geophys. Res. Lett., vol. 20, No. 10, pp. 955–958 (May 1993).

*Primary Examiner*—David P. Porta
*Assistant Examiner*—Richard Hanig
*Attorney, Agent, or Firm*—Derrick M. Reid

[57] ABSTRACT

The present system and method employs Differential Absorption Lidar (DIAL) system and method to measure gas concentration within a plume, for example, ozone density with a rocket exhaust plume when large quantities of chlorine and alumina particles are injected directly into the stratosphere by the current fleet of launch vehicles, the system generate on-resonance and off-resonance pulses prior to plume formation for measuring beyond-plume ambient return and on-resonance and off-resonance pulse during plume formation for measuring beyond-plume returns which are normalized to the ambient returns and then ratioed to indicate the absorption effect within-plume to indicate changes in gas concentrations, being well suited for analysis of environmental affect of the exhaust plumes upon the atmosphere, and particularly, for remote sensing of ozone density within the plume of Titan IV launch vehicles, but can be extended to measure other gas concentration from other types of exhaust plumes.

15 Claims, 3 Drawing Sheets

Ambient Normalized Differential Lidar (DIAL) System